(12) United States Patent
Myers et al.

(10) Patent No.: US 7,224,455 B2
(45) Date of Patent: May 29, 2007

(54) MEASURING PARTICULATE MATTER IN A FLUID

(75) Inventors: Richard Myers, Gibsonia, PA (US); Edward L. McCall, Sewickley, PA (US); Gerald F. McGowan, Park, CO (US); Edward A. Smierciak, Pittsburgh, PA (US)

(73) Assignee: Teledyne Technologies Incorporated, Thousand Oaks, CA (US)

( * ) Notice: Subject to any disclaimer, the term of this patent is extended or adjusted under 35 U.S.C. 154(b) by 188 days.

(21) Appl. No.: 10/857,548

(22) Filed: May 28, 2004

(65) Prior Publication Data

US 2005/0264809 A1    Dec. 1, 2005

(51) Int. Cl.
*G01N 21/00* (2006.01)
(52) U.S. Cl. ........................... 356/338; 356/337
(58) Field of Classification Search .............. None
See application file for complete search history.

(56) References Cited

U.S. PATENT DOCUMENTS

| | | | | |
|---|---|---|---|---|
| 3,713,743 | A * | 1/1973 | Simms | 356/338 |
| 5,131,741 | A * | 7/1992 | Zweben | 356/28 |
| 5,315,115 | A * | 5/1994 | Gerber | 250/338.1 |
| 5,456,102 | A * | 10/1995 | Moorehead | 73/1.24 |
| 5,488,469 | A * | 1/1996 | Yamamoto et al. | 356/72 |
| 5,751,423 | A * | 5/1998 | Traina et al. | 356/338 |
| 5,831,730 | A * | 11/1998 | Traina et al. | 356/336 |
| 5,999,257 | A | 12/1999 | Myers et al. | |
| 6,137,108 | A * | 10/2000 | DeThomas et al. | 250/339.07 |
| 2003/0038940 | A1* | 2/2003 | Metcalfe et al. | 356/437 |
| 2004/0155191 | A1* | 8/2004 | Stedman et al. | 250/339.12 |

OTHER PUBLICATIONS

Sick/Maihak FWE200 Datasheet, printed from www.sickmaihak.de/sickmaihak_de/products/categories/dustmonitors/fwe200/en.html on Sep. 27, 2004.

Sick/Maihak FW100 Datasheet, printed from www.sickmaihak.de/sickmaihak_de/products/categories/dustmonitors/fw100/en.html on Sep. 27, 2004.

Sick/Maihak FW100 Product Information, printed from www.sickmaihak.de/sickmaihak_de/products/categories/dustmonitors/fw100/en.toolboxpar.0002.file.tmp/PI_FW100_en_D08-00_8008903.pdf on Sep. 27, 2004.

Durag Product Sheet, printed from www.durag.com/html/ems/emsprod.html, on Sep. 27, 2004.

Process Metrix Particle Measurement Instruments, printed from <http://www.processmetrix.com/sizing.html#PCSV> <http://www.processmetrix.com/sizing.html on Sep. 27, 2004.

Richard Meyers and Edward McCall, "Analysis of Conventional Dust Density Measurement Techniques With Indications of an Improved Approach Via Forward-Scattering Angular Analysis"; presented to Air and Waste Management Association Annual Conference, Jun. 1998.

Richard Meyers, Gerald McGowan and Edward McCall, "Application and Technological Issues Associated with Continuous Monitoring of Source Particulates"; presented to Electric Utilities Environmental Conference, Tucson, AZ, Jan. 2004.

\* cited by examiner

*Primary Examiner*—Michael P. Stafira
(74) *Attorney, Agent, or Firm*—Kirkpatrick & Lockhart Preston Gates Ellis LLP

(57) ABSTRACT

A device for measuring near forward scatter caused by particulate matter in a fluid is disclosed. The device comprises, according to various embodiments, a transceiver and a reflector. The transceiver includes a light source and a detector. The reflector is positioned opposite the transceiver so that at least a portion of the fluid is present between the transceiver and the reflector. The reflector includes a front portion facing the transceiver. Optical energy from the light source incident upon the reflector is reflected towards the transceiver as a return beam of optical energy, wherein the detector senses primarily optical energy of the return beam that is scattered over a range of near forward angles by particulate matter in the fluid.

35 Claims, 12 Drawing Sheets

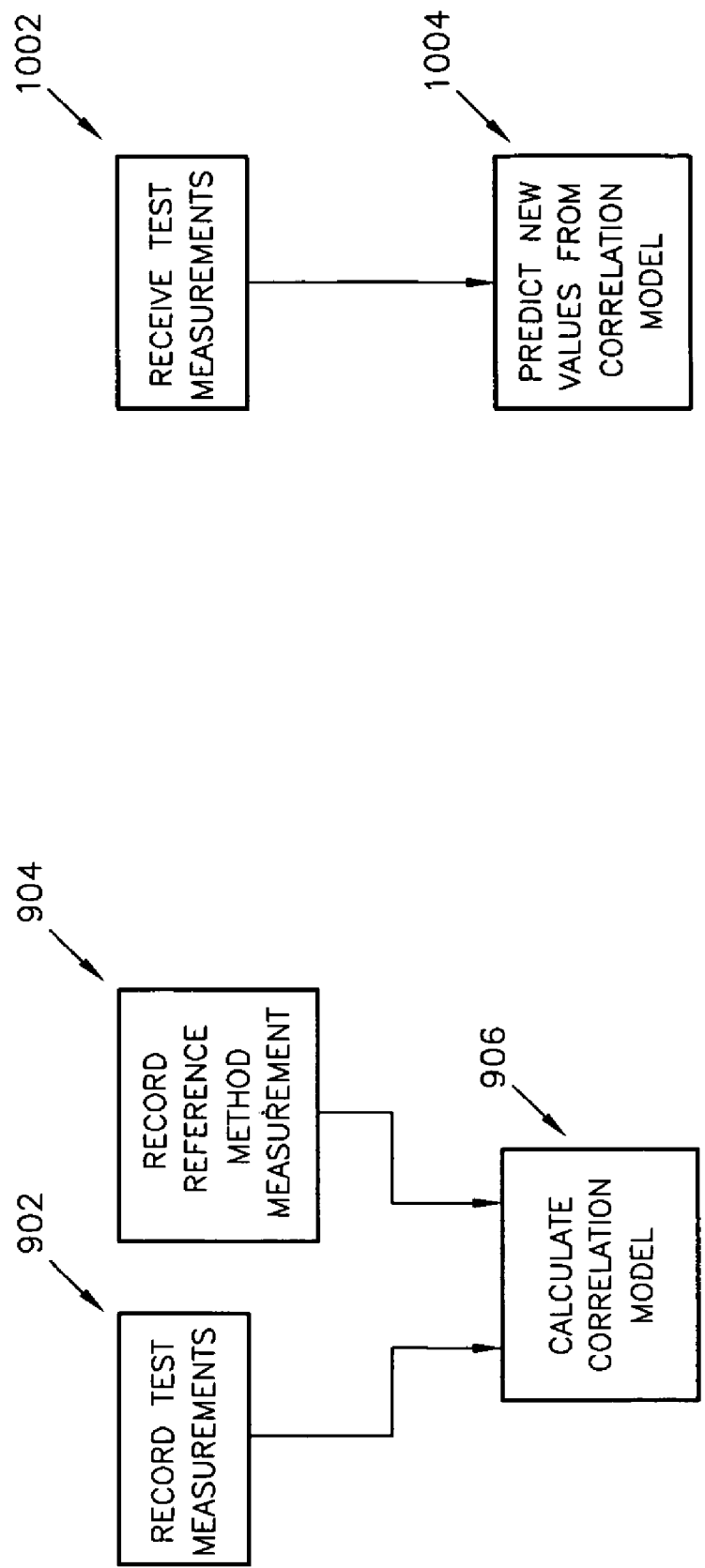

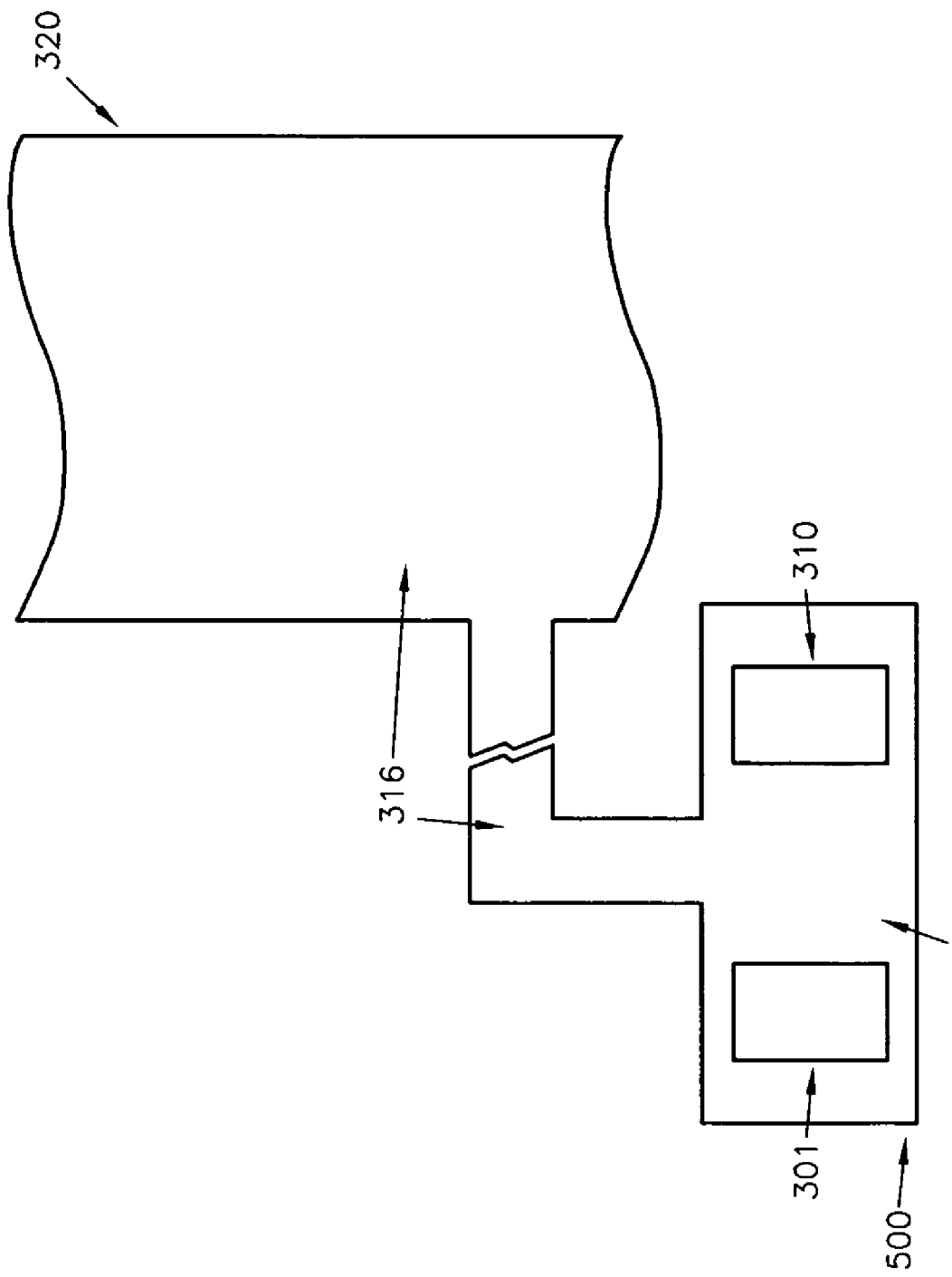

MEASURING PARTICULATE MATTER IN A FLUID

BACKGROUND OF THE INVENTION

The present invention is directed generally to the measurement of certain optical properties of the interaction of light with particulate matter in a fluid.

Power generation plants and other industrial facilities may release particulate matter into the atmosphere, especially if the facilities burn coal or other fossil fuels. Particulate matter in the flue gases generated from the burning of coal tends to be mostly spherical, solidified droplets of a variety of sizes from the metallic components of the ash in the coal. Because the particulate matter degrades air quality and reduces visibility (haze) governmental regulations require some facilities to continuously control and monitor their particulate matter emissions. Particulate mass emission rates are reported in units of weight per time (tons/yr), and are determined from particulate mass loading measurements in wt/volume (grains/standard cubic foot) and a corresponding measure of stack gas flow rate in volume/time (standard cubic feet/hour). For example, Environmental Protection Agency (EPA) or state regulations require some sources to continuously monitor the mass loading of their particulate matter emissions to prove compliance with particulate emission limitations.

Although a number of techniques are available to measure the mass loading of particulate matter emissions directly, many are costly and incapable of reliable continuous operation under field conditions. Therefore, continuous indirect measurements of optical or other properties related to the mass loading are often used in association with a correlation coefficient or a transfer function that allows calculation and output of an equivalent particulate mass loading value. Recently, the EPA implemented Performance Specification 11 (40 C.F.R. § 60, Appendix B, PS-11) to define how a particulate monitor is to be tested, and the resulting performance that is required to "certify" a particulate monitor. Certification is a term designating that a specific monitor meets the relevant EPA performance requirements for that type of analyzer and can be used to report emissions for determination of the compliance status of a given emission source. PS-11 requires that properties of particulate matter measured by continuous techniques be correlated with, or converted to, particulate mass loading and compared to a reference method (40 C.F.R. § 60, Appendix A, RM 5 or 17, for example) measurement, or series of measurements. Reference method measurements for particulate mass loading use a manual stack sampling technique and are non-continuous measurements. Several different characteristics of the interaction of light with particulate matter can be measured and correlated with particulate density, including those discussed below.

Extinction is a measure of the quantity of optical energy absorbed or scattered by particulate matter. Extinction may be measured over many wavelengths of light, however, some extinction measurements, called opacity measurements, require light spanning the visible range (400 to 700 nm). Extinction measurements are dependent on variables other than mass loading, thus reducing the accuracy of an extinction measurement as a predictor of particulate mass loading. For example, extinction is dependent on particulate shape and size, with the strongest response (for a given mass loading) occurring when particulate diameter is comparable to the wavelength of the light source. Given constant particle size distribution, shape and specific gravity, the extinction response is closely correlated with mass loading. Extinction measurements may be unusable at very low particulate mass loadings as the extinction measurement becomes difficult to make with good accuracy. The specific gravity of the particulate matter itself also affects the correlation of the extinction measurement with particulate mass loading because the optical properties of the particulate is caused by the surface area of the particulates and not the material inside the particles.

FIG. 1 depicts a prior art device 100 for measuring extinction caused by particulate matter 128 in a fluid 116, which may be an exhaust stream in an exhaust stack 120. In the device 100, a light source 102 directs a forward light beam 112 through a beam splitter 106 and lens 108 toward a reflector 110. The reflector 110 receives the forward beam 112 and reflects a return beam 114 toward a detector 104 after reflecting the return beam 114 off of a beam splitter 106. The beams 112, 114 propagate across the fluid 116 through holes 130, 132 in the stack 120. A large portion of the optical energy present in the beams 112, 114 reaches the detector 104; however, some optical energy is absorbed or scattered by the particulate matter 128 present in the fluid 116. The difference between the optical energy emitted by the light source 102 and detected by the detector 104 with a clear path (no particulate in this case) and the optical energy received by the detector 104 with particulate present in the optical path indicates the extinction caused by the particulate, thereby providing an indication of the amount of the particulate 128 present in the fluid 116. Since the beam goes across the stack and back, these optical systems are also known as double-pass.

Scatter is a measure of the quantity of optical energy that is scattered by particulate matter, or reflected off the axis of the interrogating light beam. Devices for measuring scatter may direct a light beam across an exhaust stream and measure the quantity of light that is scattered at different angles away from the beam's expected propagation direction. Backscatter refers to scatter near 180 degrees away from the projected beam, and forward scatter refers to scatter near the same angle as the projected beam. Different types of scatter measurements detected at a variety of angles, light source wavelengths and beam widths display different degrees of dependence on particulate properties other than mass loading.

Backscatter, for example, measures optical energy reflected by particulate matter in a backward direction compared to the direction of the projected beam. Backscatter is somewhat less dependent on particulate size than extinction, but still responds most strongly to very small particles. Also, unlike extinction, backscatter provides a strong response when particulate mass loading is low. Like extinction, however, backscatter techniques are very sensitive to the size, and shape of the particulate. Backscatter is also sensitive to particulate color.

FIG. 2 depicts a prior art device 200 for measuring backscatter in the fluid 216. In the device 200, the light source 202 directs a forward beam 212 through a beam splitter 206 and lens 208 across the exhaust stack 220 through holes 230, 232. An absorbing device 218, i.e. an optically black material, positioned opposite the light source 202 prevents the forward beam 212 from being reflected back to the detector. Even though the forward beam 212 is not reflected by the absorbing device 218, optical energy from the forward beam 212 is still scattered back to the detector 204 by particulate 228 present in the fluid 216 after reflecting off of beam splitter 206. The amount of optical energy received by the detector 204 is indicative of the backscatter caused by the particulate, thereby providing an indicator of the quantity of the particulate 228 in the fluid 216.

Near angle forward scatter is a measurement of the optical energy that is scattered by particulate matter in small, near forward angles. Like backscatter, near forward scatter provides a strong response when particulate mass loading is low. Unlike extinction and backscatter, however, near forward scatter provides a strong response for relatively large particulates with diameters greater than 2 microns with a visible light source. In addition, near forward scatter techniques minimize the undesirable color, size, and shape dependencies of extinction and backscatter measurements.

Existing devices for measuring near forward scatter are often complicated, expensive, and difficult to calibrate and maintain. Some require beam steering as well as active optical equipment on both sides of the exhaust stream. Many are point sampling or close coupled extractive devices and hence introduce measurement errors in applications with significant particulate stratification. Existing devices are also unable to take advantage of the strengths of other known techniques, for example extinction and backscatter. Consequently, there exists a need for a simple, efficient way to measure near angle forward scatter. In addition, there exists a need for a technique to implement multiple measurement methods with a single device so that the correlation of a group of optical measurements with particulate density can be made more independent of the size, shape, and color of the particulate matter itself than can be obtained with a single measurement.

SUMMARY OF THE INVENTION

In one general respect, the present invention is directed to a device for measuring near forward scatter caused by particulate matter in a fluid. The device, according to various embodiments, comprises a transceiver and a reflector. The transceiver includes a light source and a detector. The light source may be selected depending on the wavelengths of light to be measured and the size of the particulate, which in combination may determine the efficiency of the scattering process at any particular angle. Further a variety of light sources with different wavelengths may be used to more accurately determine the properties of the particulate. The reflector is positioned opposite the transceiver so that at least a portion of the fluid is present between the transceiver and the reflector. The reflector includes a front portion facing the transceiver. Optical energy from the light source incident upon the reflector is reflected towards the transceiver as a return beam of optical energy that is shaped such that ideally none of the main projected beam impinges directly on the detector. The light reaching the detector may be primarily the light that is scattered from the returned beam over a range of near forward angles by particulate matter in the fluid.

According to various implementations, the range of near forward angles may be between 1 and 5 degrees. Also, the front portion of the reflector may include a variety of lenses, such as a convex or concave spherical lens, a concave or convex wedge shaped lens, such wedge shaped lenses also being known as conical prisms or conical lenses. The lens may also include a central, non-transmissive portion, In addition, the device may include means for replacing the lens of the reflector with a second, or third, differently shaped lens. Also, the device may include means for replacing the reflector with a second reflector. The second reflector may be similar to the first, but the front portion or size may be different. Also, in various implementations, the return beam from the reflector may cross itself in the field of view of the detector.

The device may be mounted on an exhaust stack and, as such, may be for measuring particulate matter present in an exhaust stream in the exhaust stack. Alternatively, the device may be mounted in a diversion chamber, which may be an external measurement chamber fed from the exhaust stack but may be separate from it.

In another general aspect, the present invention is directed to a system for monitoring particulate matter in a fluid. According to various embodiments, the system may include a transceiver and a reflector assembly. The reflector assembly may be positioned opposite the transceiver so that at least a portion of the fluid is present between the transceiver and the reflector assembly. Further, the reflector assembly may include a first reflector, including a front portion facing the transceiver, such that, when the first reflector is in the path of the light beam from the light source of the transceiver, optical energy from the light source incident upon the reflector is reflected towards the transceiver as a return beam of optical energy, wherein primarily optical energy of the return beam that is scattered over a range of near forward angles by particulate matter in the fluid reaches the detector. Additionally, the reflector assembly may include a second optical device and means for cyclically moving the first reflector and the second optical device into the path of the light beam from the light source.

In various implementations, the second optical device may comprise an extinction reflector for taking extinction measurements and/or an absorbing device for taking backscatter measurements. The system may further comprise a correlation module in communication with the detector and the reflector assembly for correlating detected optical signals from the detector with particulate mass loading and/or size of the particulate matter in the fluid.

In yet another general aspect, the present invention is directed to a method of measuring mass loading of particulate matter in a fluid. The method may include, according to various embodiments, measuring near forward scatter caused by particulate matter in the fluid as well as measuring a second property of the particulate matter in the fluid. The second property may be, for example, backscatter or extinction caused by the particulate matter in the fluid. The method may further comprise calculating the mass loading of the particulate matter in the fluid based on the near forward scatter and the second and/or a third property along with other gas or process measurements. Further, there may be multiple measurements of the forward and/or backscatter measurements corresponding to different scattering angles and light sources with different predominant wavelengths.

DESCRIPTION OF THE FIGURES

Embodiments of the present invention will be described by way of example in conjunction with the following Figures, wherein:

FIGS. 7–8 and 11–13 are diagrams of various components of systems for measuring particulate matter according to various embodiments of the present invention; and FIGS. 9–10 are flow charts of methods for correlating various particulate matter measurements to a desired property according to various embodiments of the present invention.

DESCRIPTION OF THE INVENTION

Figure 3:
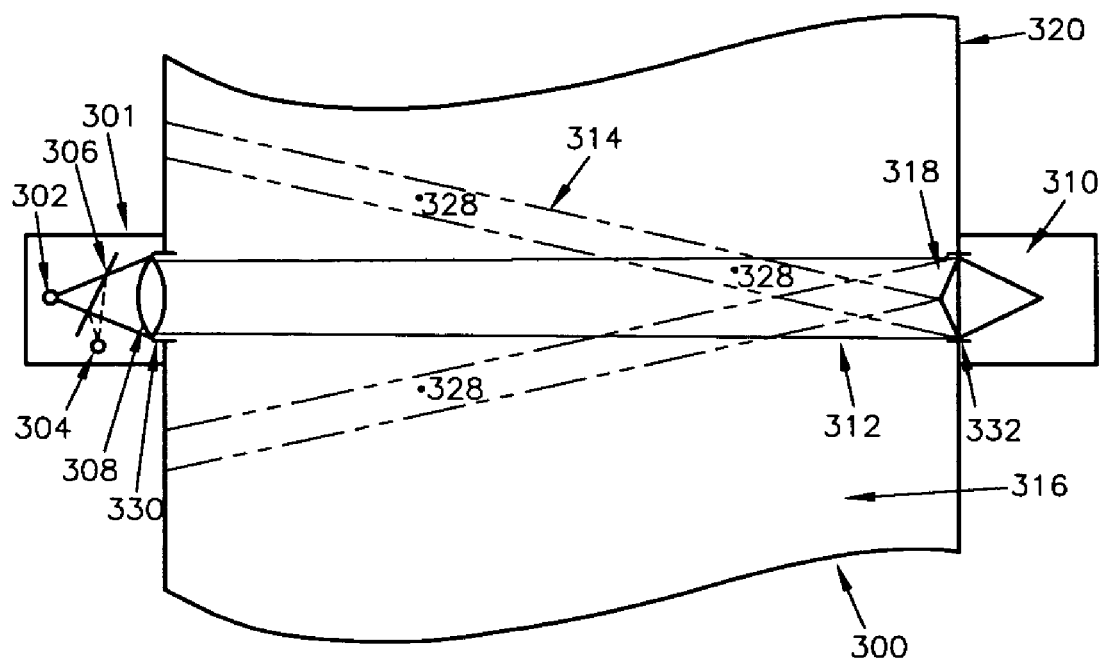
FIGS. 3–6 are diagrams of devices for measuring near forward scatter according to various embodiments of the present invention.
Figure 3A:
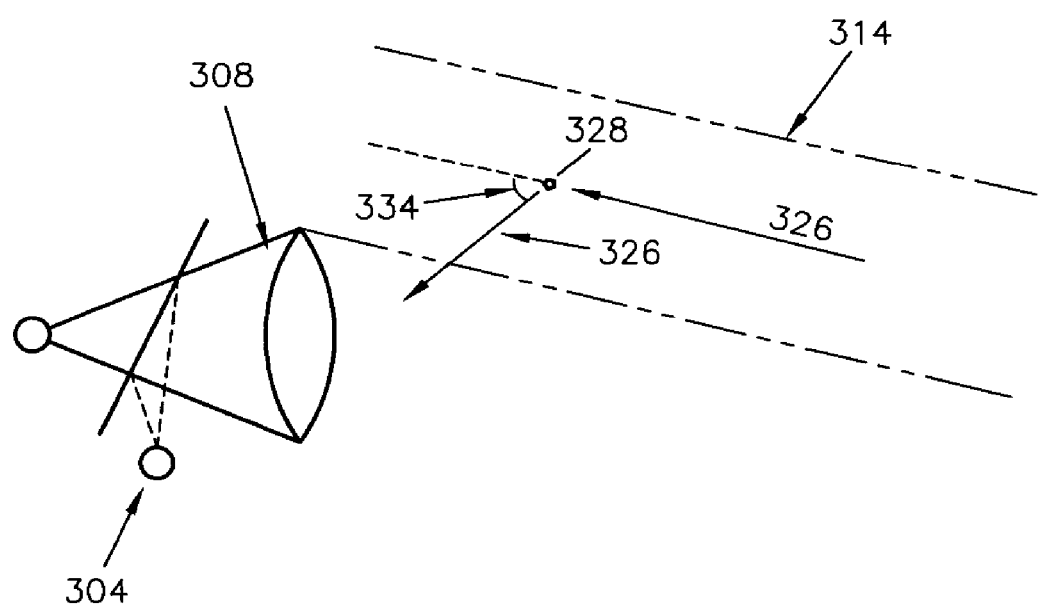
Figure 4:
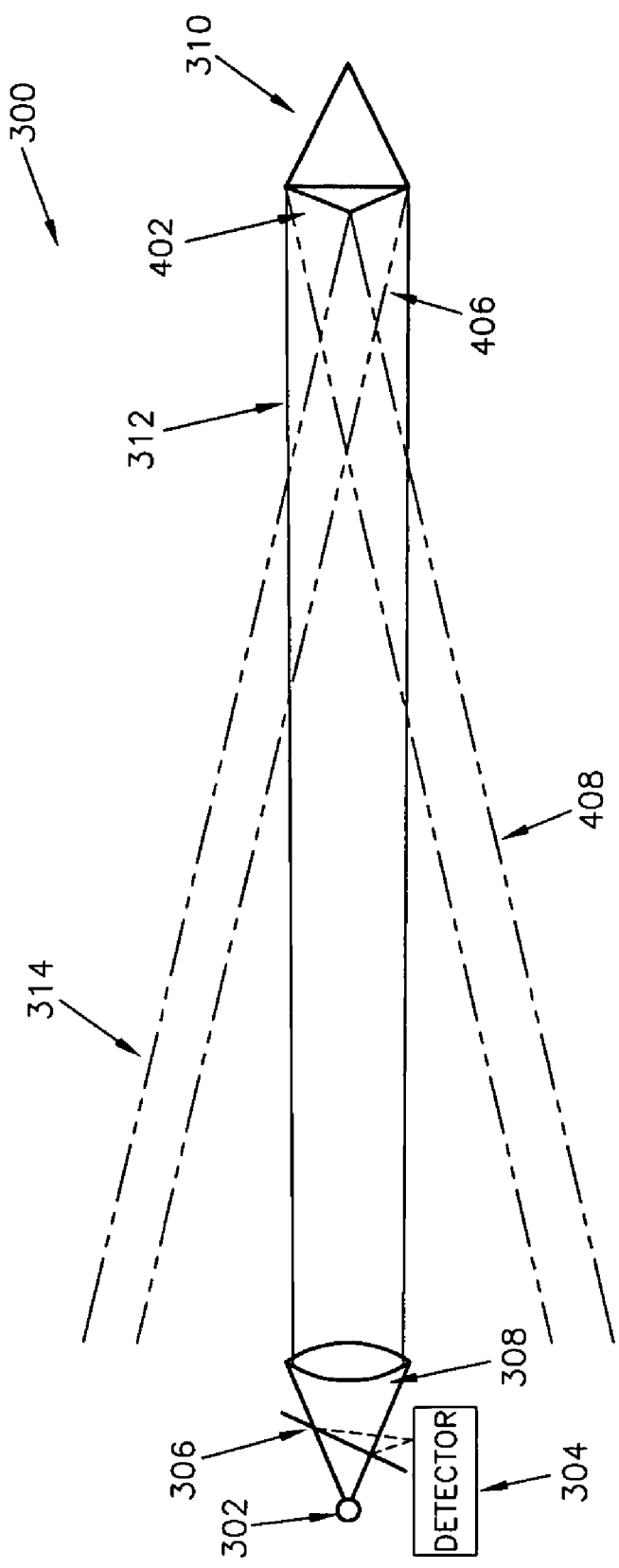

FIGS. 3, 3A and 4 depict a device 300 for measuring near forward scatter caused by particulates 328 in a fluid 316 according to various embodiments of the present invention. The device 300 may include a transceiver 301 and a reflector 310. The transceiver 301 may include a light source 302, a detector 304, a beam splitter 306 and a lens 308. The light source 302 may be any device capable of projecting a light beam such as, for example, a light emitting diode (LED), a diode or gas laser, or an incandescent source. According to one embodiment, a green LED may be used as the light source 302. The wavelength of the light source 302 may be determined based on the size of the particulates to be measured. Also, according to various aspects, the device 300 may contain more than one light source to measure scattered optical energy at multiple wavelengths. The detector 304 may be a photodiode or any other device capable of sensing optical energy reflected from the reflector 310 at a small off-axis angle and scattered by the particulate in a direction toward the lens 308 and detector 304 by the beam splitter 306.

The reflector 310 may be, for example, a total internal reflecting glass corner cube or any other device suitable for reflecting light. It will be appreciated that a corner cube has the unique property that it returns the incoming beam parallel to but displaced from the incoming beam. Therefore, using a corner cube as the reflector 310 may make the device 300 much less sensitive to small variations in alignment between the transceiver and reflector. The reflector 310 may also include a front portion 318. The front portion 318 may be, a wedge prism, as depicted in FIGS. 3 and 4, however the front portion 318 could assume other shapes according to other embodiments as described below. In various embodiments, the device 300 may be mounted on an exhaust stack 320 where the fluid 316 is part of an exhaust stream.

The device 300 may measure near forward scatter by directing a forward light beam 312 from the light source 302 toward the beam splitter 306 and lens 308, which may direct the light beam toward the reflector 310 though holes 330, 332 in the stack 320. The reflector 310 may reflect a return beam 314 in the general direction of the transceiver 301. In particular, the front portion 318 of the reflector 310 may shape the return beam 314 so that substantially all of the optical energy reaching the detector 304 has been scattered at a near forward angle by particulate 328 present in the fluid 316. In other words, but for light scattered by particulate 328 at near forward angles, no return optical energy would ideally reach the detector 304. For example, the front portion 318 of the reflector 310 may shape the return beam 314 into a hollow cone, with the hollow portion of the cone falling such that optical energy propagating in the direction of the return beam 314 does not ordinarily reach the detector 304. Optical energy scattered by particulate present in the fluid 316 at a near forward angle, though, may reach the detector 304, as shown in FIG. 3A.

FIG. 3A is an illustration of near forward scatter by particulate 328 using the device 300 of FIG. 3. The arrow 326 represents a photon propagating in the direction of the return beam 314. The photon 326 may come into contact with particulate 328. When the conditions for near forward scatter exist, the photon 326 may be deflected, or scattered, by the particulate 328 to a new propagation path differing from that of the return beam 314 by a near forward angle 334. Depending on the near forward angle 334, the photon 326 may strike the lens 308 and ultimately the detector 304. The detector 304 may be able to sense photons 326, that is, optical energy, scattered from the path of the return beam 314 at a range of near forward angles 334. In various embodiments, the range of near forward angles 334 visible to the detector 304 may be between 1 and 5 degrees, though any range of near forward angles may be used.

In the device 300, the front portion 318 of the reflector 310 may be a lens 402. The lens 402 may be a convex wedge shaped lens, or a conical prism, as shown in FIG. 4, and may modify the return light beam 314 to form two contiguous cones, 406 and 408 which are adjoined by their apex angles. The cone 408 may be hollow, preventing un-scattered optical energy of the return beam 314 from reaching the detector 304. Scattered optical energy from the return beam 314, however, may reach the detector 304 when it is scattered over the range of scattering angles 334 visible to the detector 304. The range of scattering angles 334 visible to the detector 304 may be dependent on the shape of the cones 406 and 408 and may be modified by changing the wedge angle of the lens 402. Also, because the cones 406 and 408 cross over each other within the field of view of the detector 304, the quantity of scattered optical energy visible to the detector 304 may be maximized.

Figure 5:
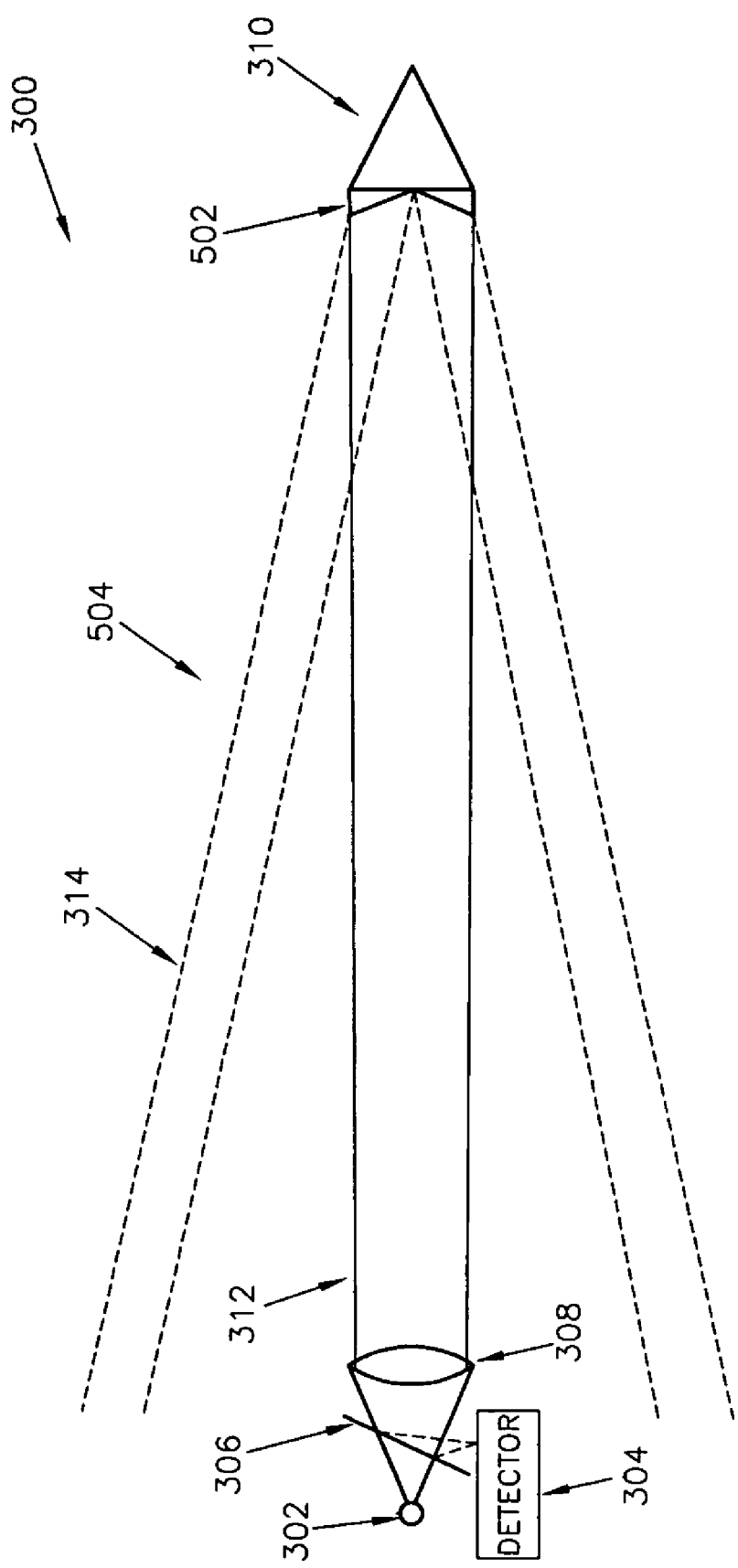

According to other various embodiments of the present invention, the front portion 318 of the reflector 310 may be of various other shapes. For example, FIG. 5 is a diagram of the device 300 having a different configuration for the front portion 318 of the reflector 310 than in FIG. 4. In FIG. 5, the front portion 318 of the reflector 310 includes a concave wedge shaped lens 502, which may modify the shape of the return beam 314, as shown in FIG. 5, causing it to form one hollow cone 504. FIG. 5 shows that the hollow portion of the cone 504 falls around the lens 308. Thus, un-scattered optical energy from the return beam 314 may be prevented from reaching the detector 304. Optical energy from the return beam 314, however, may reach the detector 304 if it is scattered by particulate matter (not shown) in the fluid 316 over a range of scattering angles 334 visible to the detector 304. The range of scattering angles 334 visible to the detector 304 may be related to the shape of the cone 504, and may be modified by changing the wedge angle of lens 502.

In some conditions, optical energy may be reflected by the lens 402 or 502 directly towards the transceiver 301. Also, if the apex of lens 402 or 502 and/or the apex of the reflector 310 are not both aligned with the optical axis of the transceiver 301, a cone of un-scattered light may be directed toward the transceiver 301. As such, the transceiver 301 may be shielded from extraneous un-scattered optical energy by creating a black or otherwise non-transmissive portion (not shown) on the front portion of the lens 402 or 502. In this way, near forward angle scattered optical energy detected by the detector 304 will not be overwhelmed by un-scattered optical energy directed towards the transceiver 301.

Figure 6:
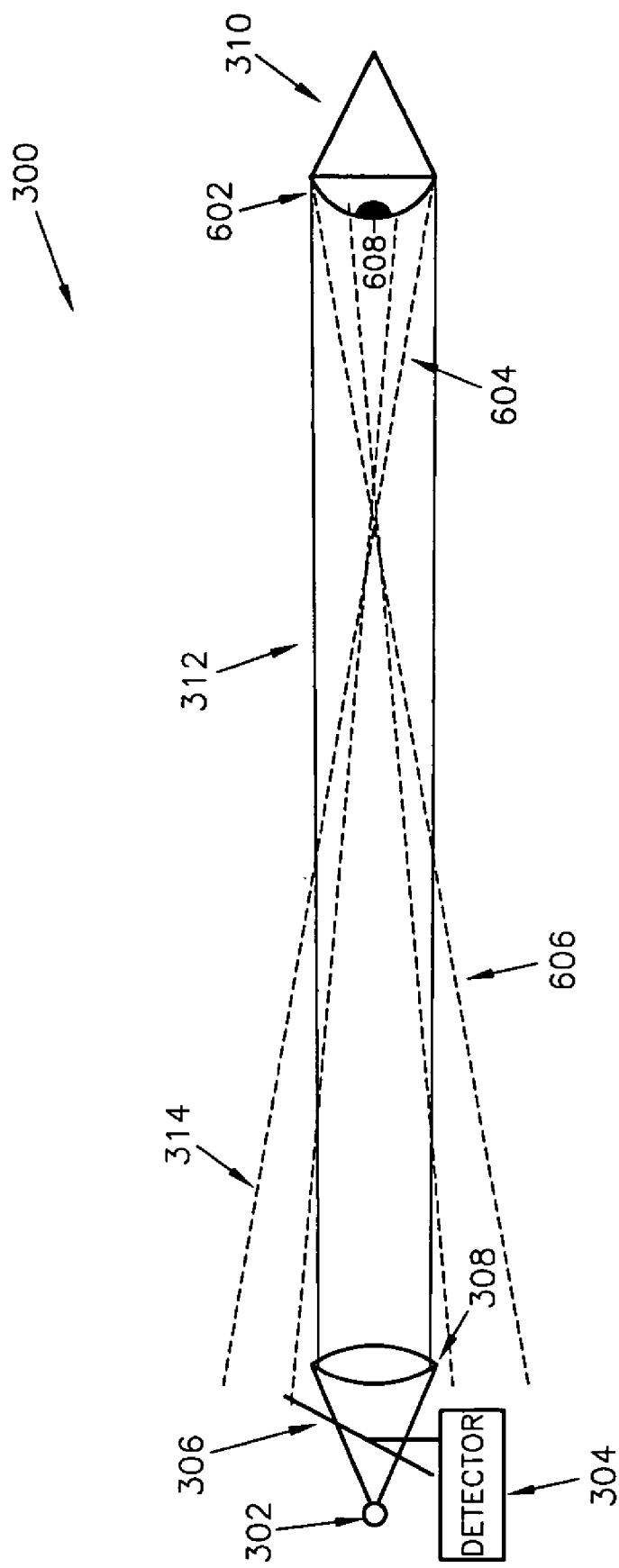

According to other various embodiments of the present invention, the front portion 318 of the reflector 310 may assume yet other shapes. FIG. 6 is a diagram of the device 300 having a different configuration for the front portion 318 of the reflector 310 than in FIG. 4 or FIG. 5. In FIG. 6, the front portion 318 of the reflector 310 includes a convex spherical lens 602. According to various embodiments, the convex lens 602 modifies the shape of the return beam 314, as shown in FIG. 6, causing it to form two adjoining cones of light 604 and 606. In some embodiments, the front portion of the lens 602 may include a black or otherwise non-transmissive portion 608, which may cause the cone 606 to be hollow, blocking the optical energy that would otherwise have fallen on lens 308 and ultimately the detector 304. This may prevent un-scattered optical energy of the return beam 314 from reaching the detector 304. Thus the primary optical energy falling on the detector 304 may be that which has been scattered from the return beam 314 by a range of near forward angles 334. The range of near forward scattering angles 334 visible to the detector 304 may be modified by changing the focal length of lens 602, or the size and location of the opaque mark 608.

The device 300, according to various embodiments, is an improvement over the devices 100, 200 above because it makes a near forward scatter measurement using many of the same components as a conventional double-pass extinction measurement instrument, thereby providing substantial cost savings and the ability to use the same transceiver for extinction and for forward scatter and backscatter measurements. As discussed above in more detail, near forward scatter provides a stronger response than extinction when particulate mass loading is low, and provides a stronger response than back-scatter or extinction for relatively large particulates. In addition, near forward scatter is less dependent on color and size than either of these methods. The device 300 is also an improvement over existing devices for measuring near forward scatter because it involves fewer moving parts, and is easier to calibrate. For example, some existing near forward scatter measuring devices require a beam steering apparatus. Not only does this add moving parts to the device, but it also makes calibration more complex.

Figure 1:
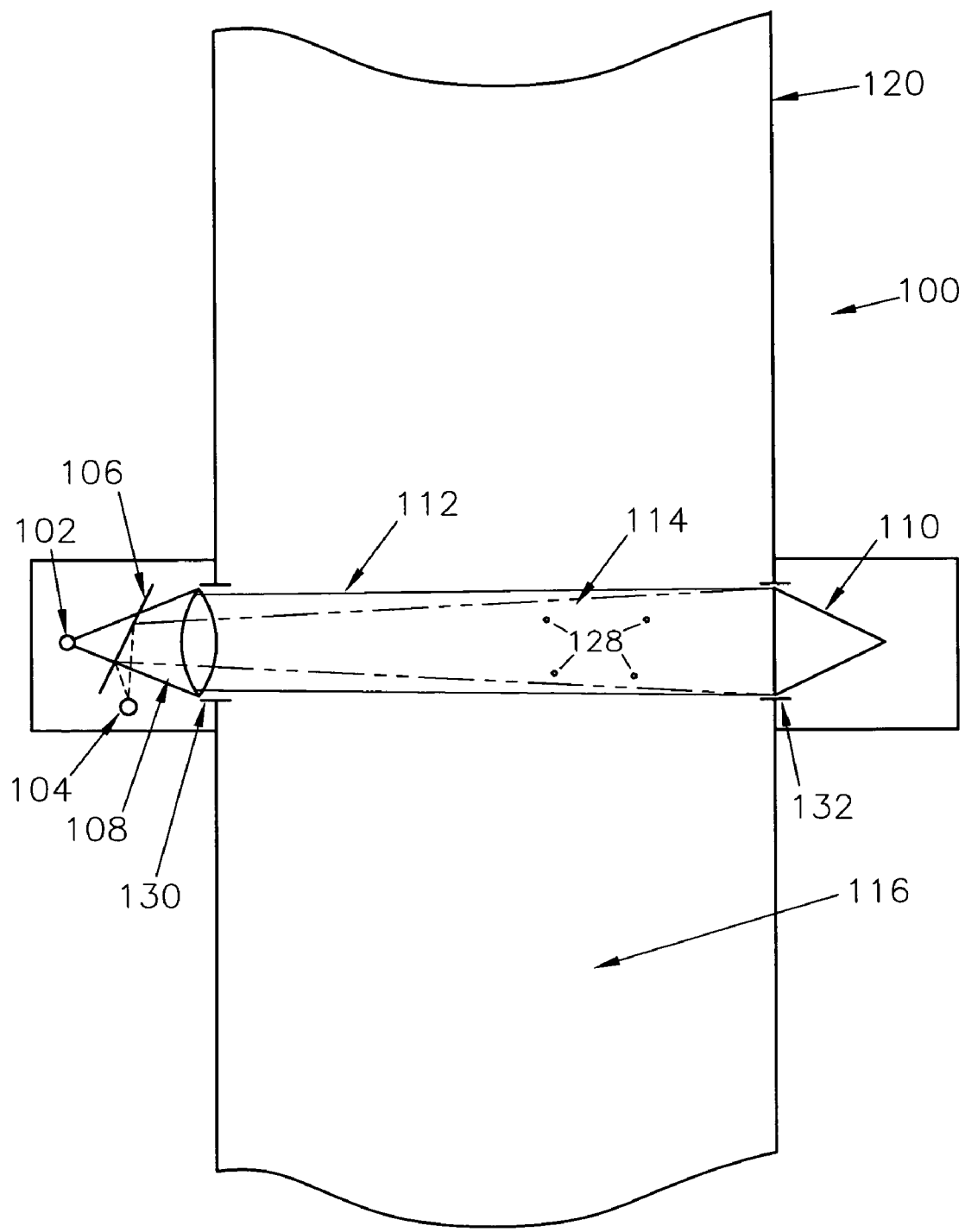
FIG. 1 is a diagram of a prior art device for measuring extinction.
Figure 2:
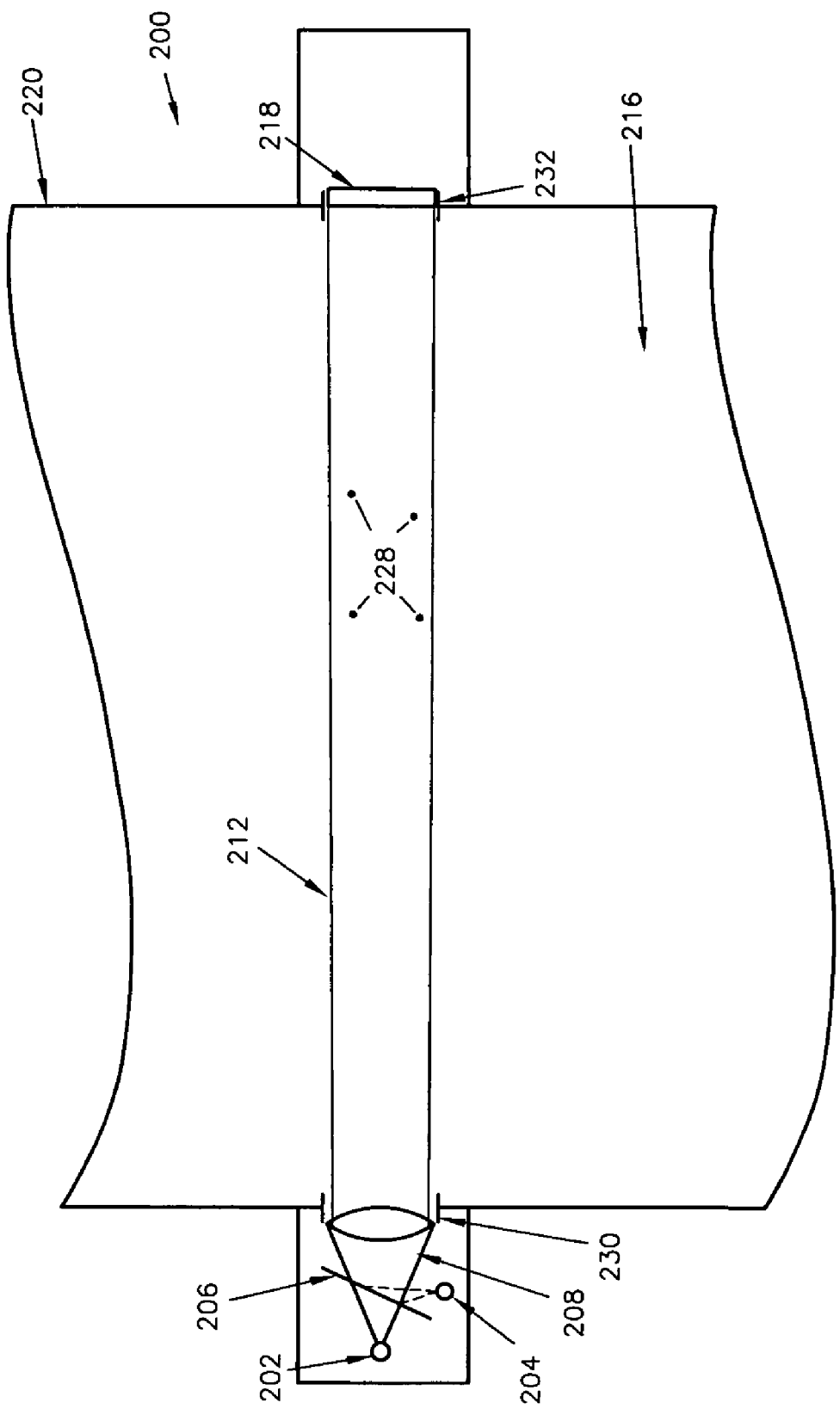
FIG. 2 is a diagram of a prior art device for measuring back scatter.
Figure 7:
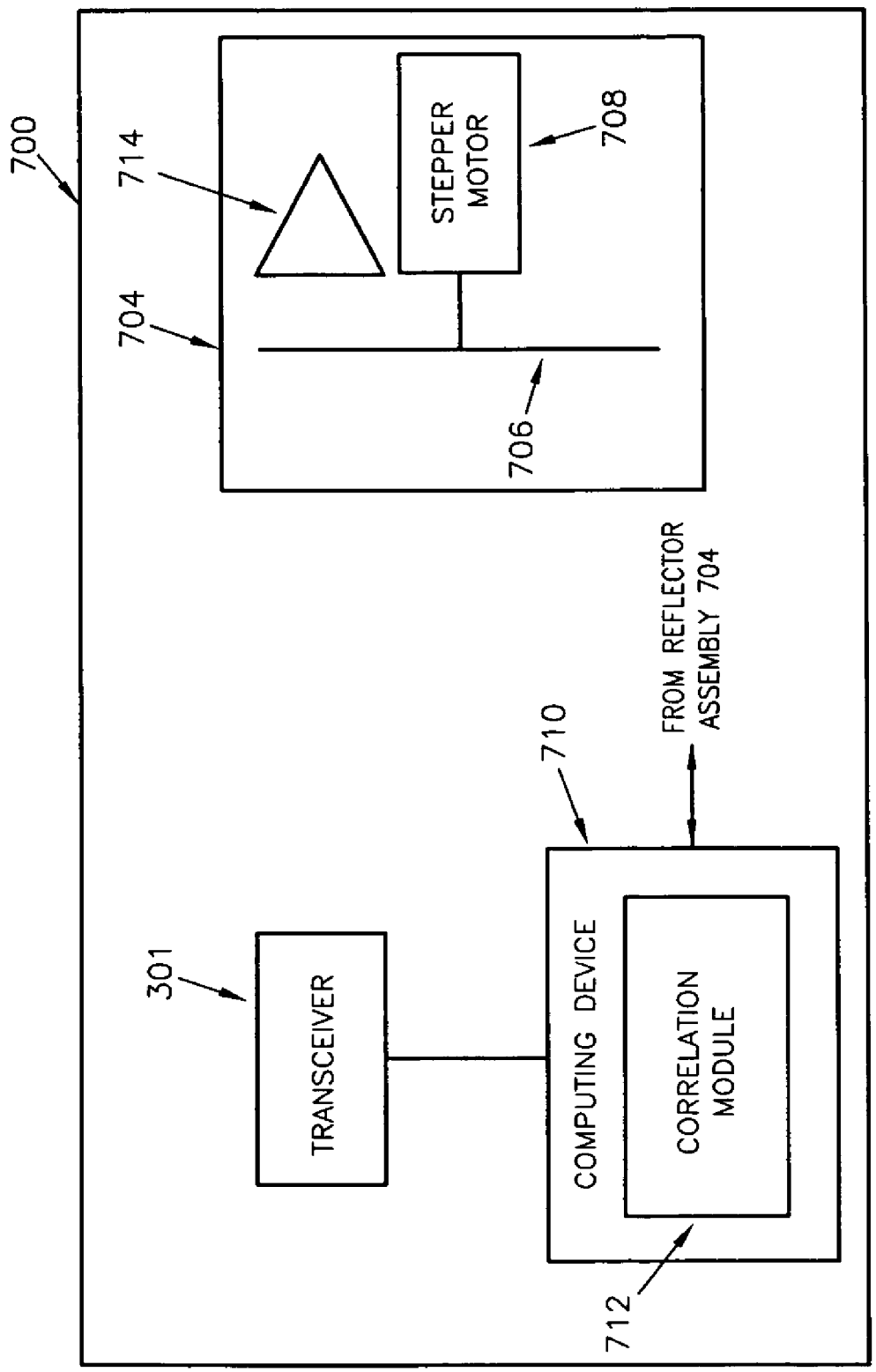
Figure 8:
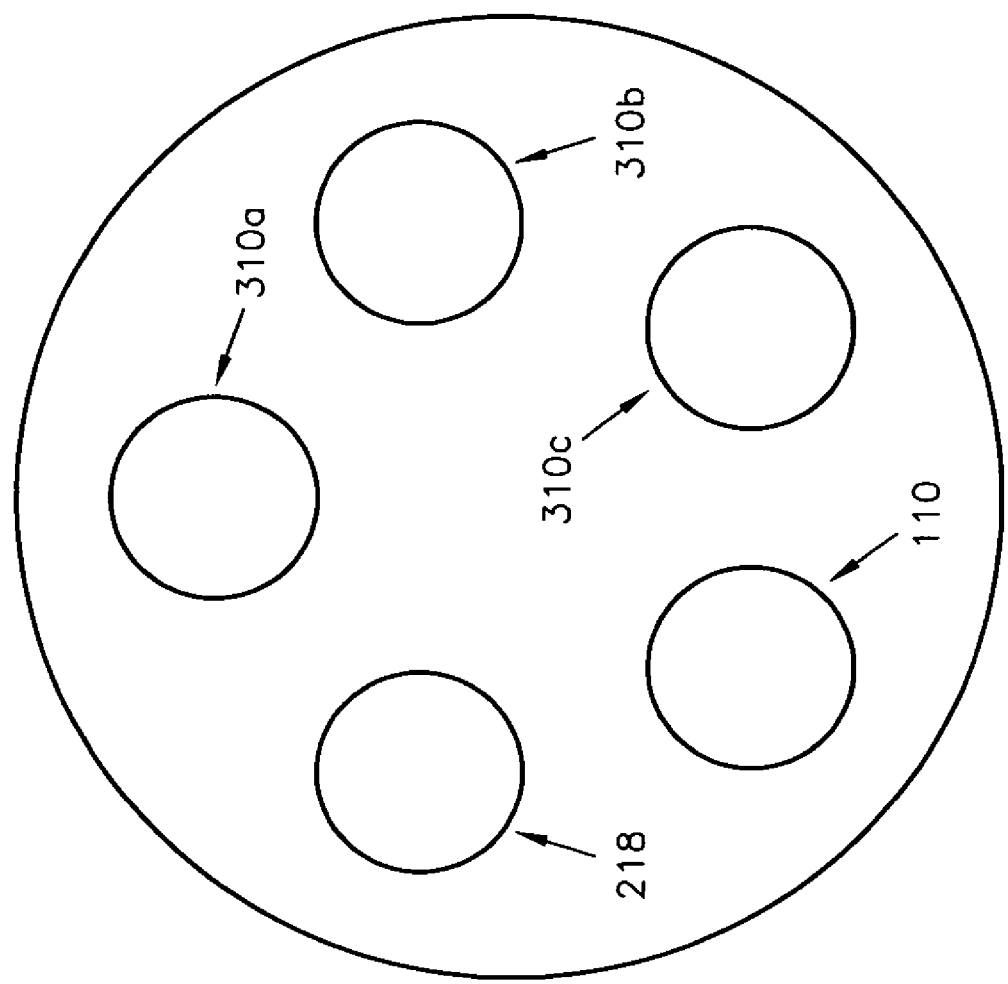

Various embodiments of the present invention are also directed to a system 700 for taking various different measurements of particulate matter in a fluid 116, as shown in FIGS. 7 and 8. The system 700 may take measurements using multiple techniques over ranges, for example, of optical wavelengths, and scattering angles. The system 700 is similar to the devices 300 of FIGS. 4–6, except that the system 700 includes a reflector assembly 704 that permits the measurement of near forward scatter of the particulate matter in the fluid 116, as well as other measurements of particulate matter in a fluid, including, for example, extinction and/or backscatter measurements. In order to achieve this, the reflector assembly 704, according to various embodiments, may comprise a wheel 706 having different front portions (lenses) that are positioned in front of a reflector 714, or having different reflectors with front portions thereon including at least one near forward scatter reflector 310, such as different ones of the reflectors 310 shown in FIGS. 4–6, as well as an extinction reflector 110, such as described above in conjunction with FIG. 1, and/or a backscatter absorbing device 218, such as described above in conjunction with FIG. 2. In FIG. 8, three near forward scatter reflectors or front portions thereof $310_{a-c}$ are shown, although according to various embodiments a different quantity of different near forward scatter reflectors 310 could be included on the wheel 706. The near forward reflectors $310_{a-c}$ may all be different from one another, such as variations on the reflectors shown in FIGS. 4–6, to thereby provide different measurements. For example, the near forward reflectors $310_{a-c}$ may be configured to allow the measurement of near forward scatter over different ranges of scattering angles. The reflector assembly 704 may include a stepper motor 708 or other electromechanical positioning device for rotating the wheel 706. In various other embodiments, the wheel 706 may have various optical devices, for example, a front portion 318, a backscatter absorbing device 218, or no device at all. In these various embodiments, rotating the wheel may cause the various optical devices to be placed in front of a stationary reflector 310.

In operation, as the wheel 706 rotates, the various reflectors 310, 110 and/or absorbing device 218 are cyclically rotated into the path of the beam from the transceiver 301. The detector 304 may detect the various amounts of optical energy incident on the transceiver 301 and within the angle of view of the detector for each different type of reflector 310, 110 or absorbing device 218. In this way, measurements to determine the mass loading of particulate in the fluid may be collected for near forward scattering measurement techniques, as well as for extinction and/or backscattering techniques. The combination of data from these different measurements techniques may provide an even more accurate indication of the mass loading of particulate in the fluid. Additionally, combining near forward scatter measurements taken over different ranges of scattering angles and with different light sources may give an improved indication of particulate size and mass loading.

In addition to the components described above, the system 700 may include a computing device 710 in communication with the detector 304 of the transceiver 301 and the reflector assembly 704. The detected light measurements from the detector 304 for the various reflectors/absorbers of the reflector assembly 704 may be communicated to the computing device 710, which may also receive timing information from the reflector assembly 704 to synchronize the various amounts of detected light from the detector 304 to the reflector 310, 110 or absorbing device 218 in the path of the beam at the time. Based on this information, the computing device 710 may, for example, correlate extinction, backscatter and multiple near angle forward scatter optical measurements with particulate mass loading.

The computing device 710 may include, for example, one or a number of networked personal computers, laptops, servers, microprocessors, micro-controllers, etc. The computing device 710 may also include a correlation module 712 for performing the correlation calculations. The correlation module 712 may be implemented as software code to be executed by a processor (not shown) of the computing device 710 using any type of computer instruction type suitable such as, for example, Java, C, C++, Visual Basic, etc., using, for example, conventional or object-oriented techniques. The software code may be stored as a series of instructions or commands on a computer readable medium, such as a random access memory (RAM), a read only memory (ROM), a magnetic medium such as a hard-drive or a floppy disk, or an optical medium such as a CD-ROM.

The correlation module 712 may convert the results of one or more measurements into a calculated value of mass loading based on a correlated model. Equation 1, below, describes a model for correlating measurements of various particulate matter properties to mass loading, or another desired property that the correlation module 712 may employ to perform the correlation according to various embodiments.

$$y(x_1, x_2, x_3, \ldots x_n) = a_1 {}^*x_1 + a_2 {}^*x_2 + a_3 {}^*x_3 + \ldots + a_n {}^*x_n \quad (1)$$

In equation 1, the function y may represent the mass loading prediction of the model. The dependent variables $x_1 - x_n$ may represent measurements of particular properties of particulate matter. For example, $x_1$ may represent an extinction or opacity measurement, and $x_2$ may represent a backscatter measurement. The variables $x_3$ through $x_n$ may represent near angle forward scatter measurements. According to various embodiments, different near angle forward scatter measurements may be taken using different configurations of the system 700. Also, different near angle forward scatter measurements may measure near angle forward scatter over different ranges of scattering angles.

Still referring to equation 1, the variables $a_1$–$a_n$ may represent correlation coefficients for dependent variables $x_1$–$x_n$. For example, $a_1$ may be the correlation coefficient for an extinction measurement, $a_2$ may be the correlation coefficient for a backscatter measurement, and $a_3$–$a_n$ may be the correlation coefficients for near angle forward scatter measurements. The correlation coefficients $a_1$–$a_n$ may be developed using any suitable multivariate technique, including, for example, a partial least squares technique. It is noted that the dependent variables $x_1$–$x_n$ may relate to any measurement of a property of particulate matter, and should not be limited to the measurement associations discussed above. In addition, there may be different sets of correlation coefficients for different fuels, which when combusted provide different particle characteristics, and for different emission control equipment characteristics.

According to various embodiments, the correlation coefficients $a_1$–$a_n$ may be developed in relation to a corresponding set of optical measurements and mass loading measurements provided by a reference method or equivalent. The reference method may be, for example, the method set forth at 40 C.F.R. Part 60, Appendix A, Reference Method 5 or 17. A test set of simultaneous readings may be taken from the reference method and the various continuous methods, $x_1$–$x_n$. The test set may include readings taken over a range of process conditions. Correlation coefficients $a_1$–$a_n$, correlating the continuous methods to the reference method, may then be calculated from the test set using any multivariate technique, including those discussed above. The test set may take as input, $x_1$–$x_n$, any combination of continuous methods that measure a property of particulate matter, including, for example, the extinction, backscatter, and near angle forward scatter methods described above.

Equation 2 describes an alternative model that may be employed by the correlation module 712 to correlate various particulate matter property measurements to mass loading.

$$y(z_1, z_2, z_3, \ldots, z_n) = a_1 * z_1(x_1) + a_2 * z_2(x_2) + a_3 * z_3(x_3) + \ldots + a_n * z_n(x_n) \quad (2)$$

In equation 2, $z_{1-n}$ may represent nonlinear functions of the $x_{1-n}$ dependent variables. For example, the functions $z_{1-n}$ may have polynomial, exponential, or logarithmic forms. A polynomial instance of $z_1$ may be represented by equation 3 below.

$$z_1(x_1) = b_0 + b_1 * x_1 + b_2 * x_1^2 + b_3 * x_1^3 + b_4 * x_4 + b_5 * x_1^5 \quad (3)$$

An exponential instance of $z_1$ may be represented by equation 4 below.

$$z_1(x_1) = b_1 * e^{b0 \times 1} + b_2 \quad (4)$$

A logarithmic instance of $z_1$ may be represented by equation 5 below.

$$z_1(x_1) = b_1 * \ln(b_2 x_1 + b_3) + b_0 \quad (5)$$

It is noted that the coefficients $b_n$ of the various instances of $z_1$ described above need not be equal to the coefficients of $z_2$–$z_n$. Correlation coefficients $a_1$–$a_n$ and the functions $z_1$–$z_n$ may be found by taking a test set similar to the one described above, and again performing a correlation using any suitable multivariate method, such as for example, partial least squares.

FIG. 9 is a flowchart of a process flow through the correlation module 712 for developing a correlation model according to various embodiments of the present invention. At block 902, the correlation module 712 or other computing devices not part of the monitoring system 700 may receive from the system 700 one or more test measurements of particulate properties in the fluid 316. The test measurements may include, for example, near forward scatter, backscatter, and extinction as described above, at different scattering angles and wavelengths of light. At block 904, the correlation module 712 or other computing devices not part of the monitoring system 700 may receive as input the results of a reference method measuring the mass loading of particulate present in the fluid 316. In various embodiments, the reference method may also be implemented by the system 700. The reference method results may be acquired at approximately the same time as the test measurements of particulate properties. The steps of blocks 902 and 904 may be repeated as many times as desired to create a set of test data over a range of operating conditions. At block 906, the correlation module 712 or other computing devices not part of the monitoring system 700 may process data from the set of test data to calculate the correlation model. The correlation model may take the form of Equations 1 or 2 above, for example. The correlation model may be developed by, for example, solving for the correlation coefficients $a_3$–$a_n$, and/or nonlinear equations $z_1$–$z_n$ of Equations 1 or 2 above.

FIG. 10 is a flowchart of a process flow through the correlation module 712 for implementing a correlation model according to various embodiments of the present invention. At block 1002, the correlation module 712 may receive from the system 700 one or more measurements of particulate properties in the fluid 316. At block 1004, the model developed above with reference to FIG. 9 may be applied by, for example, entering particulate properties into the Equations 1 or 2 as dependent variables $x_1$–$x_n$. Solving the equation may yield a measurement of mass loading on a continuous basis.

In the description above, the near forward angle scatter devices 300 were disclosed as directly measuring the particulate matter in the fluid 316 in an exhaust stack 320. According to other embodiments, however, the near forward scatter device 300 could be used to measure the particulate matter in a diverted portion of the exhaust stack 320, as shown in FIG. 11. In such an embodiment, a portion of the fluid 316 may be diverted to a chamber 500. The device 300 may measure the particulate matter in the chamber 500, which may be indicative of the particulate matter mass loading in the fluid 316 in the exhaust stack 320. Such a diverted portion of the main fluid flow stream may be heated to vaporize any entrained water droplets, or otherwise arranged to accommodate very high temperature gas streams or very large or small stack/duct diameters, or to pull the gas stream to a more convenient or protected measurement environment. Isokinetic sampling of the main stream may be necessary if a representative particulate sample of the main gas stream is to be obtained.

Figure 12:
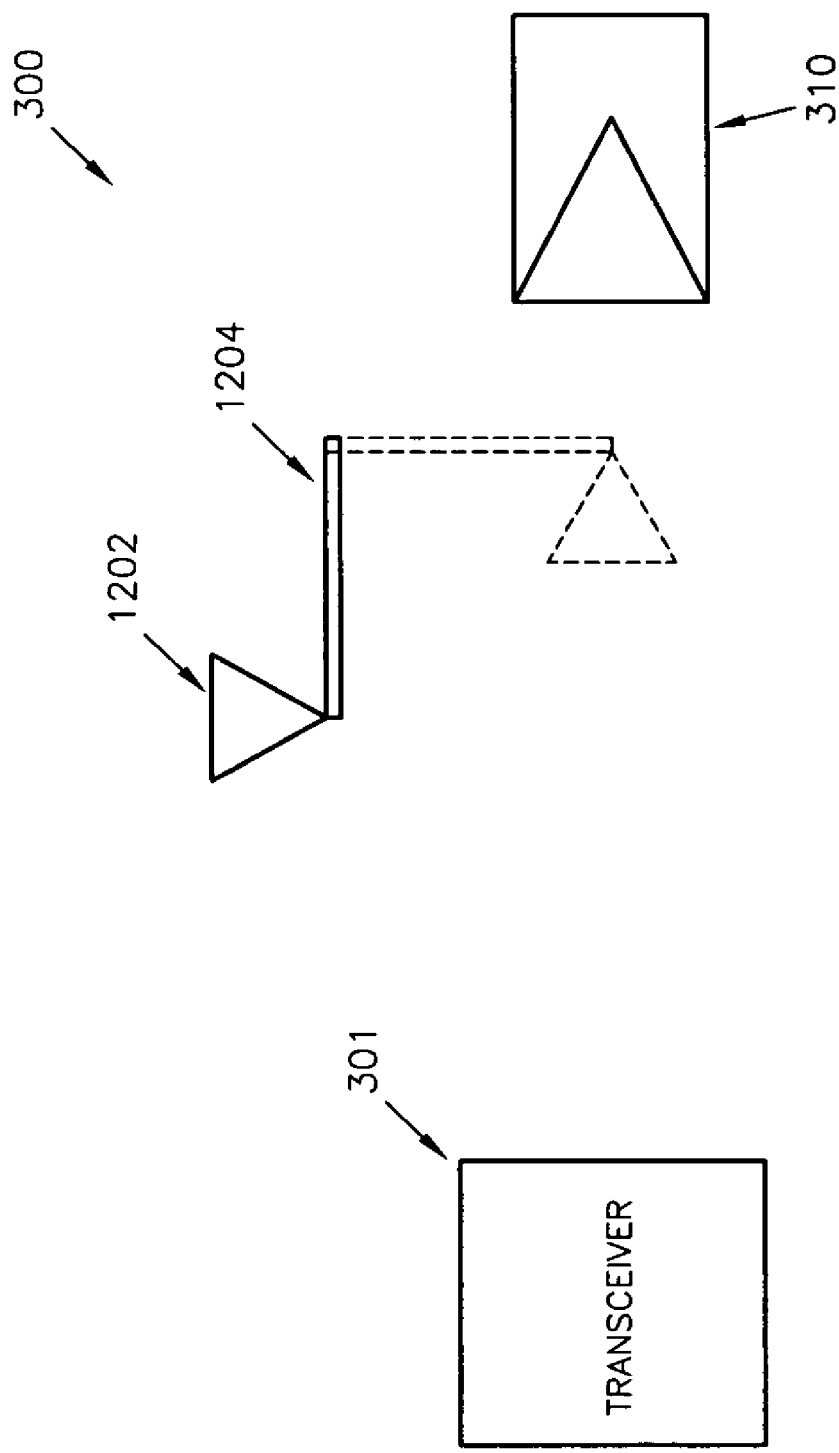

Also, according to other embodiments in the system 700 for taking different types of optical measurements, instead of using a wheel 706 to move the various reflectors/absorbers into the path of the beam, one or a number of swing arms 1204 may be used, as shown in FIG. 12. The one or more swing arms 1204 may be operated by a stepper motor or other electromechanical positioning device (not shown)

which may be controlled by the computing device 710. A near angle forward reflector 310, an extinction reflector 110 or an absorbing device 218 may be mounted on each swing arm 1204 and lowered into the path of the beam when the swing arm 1204 is lowered. According to various other embodiments, various other optical devices, for example, a front portion 318, or a backscatter absorbing device 218, may be mounted on swing arms 1204. Lowering the swing arms 1204 may cause one or more of the various other optical devices to be placed in front of one stationary reflector 310.

Figure 13:
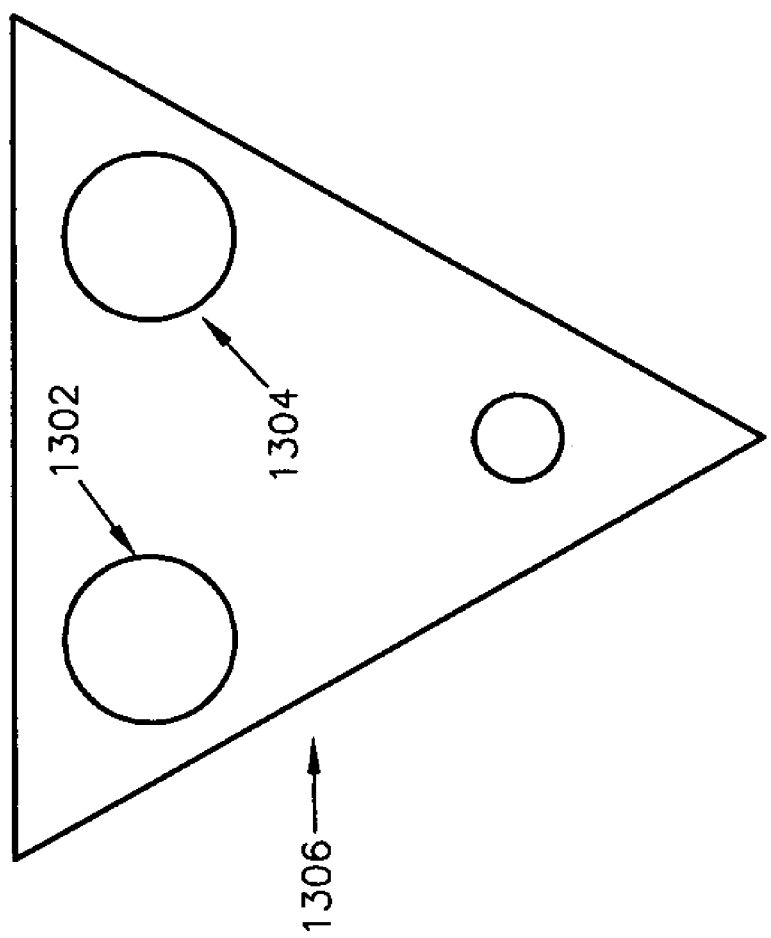

As shown in FIG. 13, the system 700 may be calibrated by placing one or more optical calibration devices 1302, 1304, which may be, for example, filters of varying reflectivity, into the path of the beams 312, 314. The optical calibration devices 1302, 1304 may simulate known conditions where a certain amount of particulate is present. For example, if an optically black filter is used as one of the calibration devices 1302, 1304, then none of the light from the light source should reach the transceiver 301, simulating a scatter measurement with no particulate present. Conversely, if a somewhat reflective filter is used as one of the calibration device 1302, 1304, then a substantial portion of the light may reach the transceiver 301, simulating an extinction measurement with particulate present. Other filters with intermediate reflectivity may also be used to simulate other conditions.

Optical calibration devices 1302, 1304 may be placed into the path of beams 312, 314 by a variety of methods. For example, the optical calibration devices 1302, 1304 may be mounted on swing arms and manipulated into the beam path by the same method described above in conjunction with reflector 1202 and swing arm 1204. Also, optical calibration devices 1302, 1304 may be mounted on a calibration plate 1306 as shown in FIG. 13. The calibration plate 1306 may be rotated into the beam path by a stepper motor or other electromechanical positioning device (not shown) in a manner similar to that described above with reference to wheel 706.

While several embodiments of the invention have been described, it should be apparent that various modifications, alterations and adaptations to those embodiments may occur to persons skilled in the art. For example, various particulate matter measurement methods may be added or subtracted. It is therefore intended to cover all such modifications, alterations and adaptations without departing from the scope and spirit of the present invention as defined by the appended claims.

We claim:

1. A device for measuring near forward scatter of light caused by particulate matter in a fluid, the device comprising:
   a transceiver, the transceiver comprising:
      a light source for projecting a light beam through the fluid; and
      a detector positioned on the same side of the fluid as the light source; and
   a reflector positioned opposite the transceiver so that at least a portion of the fluid is present between the transceiver and the reflector, wherein the reflector includes a front portion facing the transceiver, such that optical energy from the light source of the transceiver incident upon the reflector is reflected towards the transceiver as a return beam of optical energy, wherein primarily optical energy of the return beam that is scattered over a range of near forward angles by particulate matter in the fluid reaches the detector.

2. The device of claim 1, wherein the range of near forward angles is between 1 and 5 degrees.

3. The device of claim 1, wherein the front portion of the reflector includes a lens.

4. The device of claim 3, wherein the front portion of the reflector includes a convex lens including a non-transmissive central portion.

5. The device of claim 3, wherein the front portion of the reflector includes a concave wedge shaped lens.

6. The device of claim 5, wherein the concave wedge shaped lens includes a non-transmissive central portion.

7. The device of claim 3, wherein the front portion of the reflector includes a convex wedge shaped lens.

8. The device of claim 7, wherein the convex wedge shaped lens includes a non-transmissive central portion.

9. The device of claim 1, wherein the transceiver further comprises a second light source with a wavelength different than a wavelength of the first light source.

10. The device of claim 3, wherein the lens includes a non-transmissive central portion.

11. The device of claim 3, further comprising means for replacing the lens of the reflector with a second, differently shaped lens.

12. The device of claim 3, further comprising means for replacing the reflector with a second reflector.

13. The device of claim 12, wherein the second reflector includes a front portion facing the transceiver, such that optical energy from the light source of the transceiver incident upon the second reflector is reflected towards the transceiver as a return beam of optical energy, wherein primarily optical energy of the return beam that is scattered over a second range of near forward angles by particulate matter in the fluid reaches the detector.

14. The device of claim 1, wherein the return beam crosses itself in the field of view of the detector.

15. The device of claim 1, wherein the light source is selected from the group consisting of a light emitting diode, a laser diode, and an incandescent source.

16. The device of claim 1, wherein the device is mounted on an exhaust stack and is for measuring particulate matter present in an exhaust stream in the exhaust stack.

17. The device of claim 1, wherein the device is mounted in a diversion chamber and is for measuring particulate matter present in a fluid that has been diverted from an exhaust stream into the diversion chamber.

18. A system for monitoring particulate matter in a fluid comprising:
   a transceiver, comprising:
      a light source for projecting a light beam through the fluid; and
      a detector; and;
   a reflector assembly positioned opposite the transceiver so that at least a portion of the fluid is present between the transceiver and the reflector assembly, the reflector assembly comprising:
      a first reflector including a front portion facing the transceiver, such that, when the first reflector is in the path of the light beam from the light source, optical energy from the light source incident upon the reflector is reflected towards the transceiver as a return beam of optical energy, wherein primarily optical energy of the return beam that is scattered over a range of near forward angles by particulate matter in the fluid reaches the detector;
      a second optical device; and means for cyclically moving the first reflector and the second optical device into the path of the light beam from the light source.

19. The system of claim 18, wherein the second optical device includes an extinction reflector.

20. The system of claim 18, wherein the reflector assembly further indudes an absorbing device, and wherein the means for cyclically moving is further for cyclically moving the first reflector, the second optical device and the absorbing device into the path of the light beam from the light source.

21. The system of claim 18, wherein the second optical device includes an absorbing device.

22. The system of claim 18, further comprising a correlation module in communication with the detector and the reflector assembly.

23. The system of claim 22, wherein the correlation module is for correlating detected optical signals from the detector with particulate mass concentration in the fluid.

24. The system of claim 22, wherein the correlation module is for correlating detected optical signals from the detector with particle size for the particulate matter in the fluid.

25. A method of measuring mass loading of particulate matter in a fluid within an exhaust stream, the method comprising:
    measuring near forward scatter caused by particulate matter in the fluid, wherein the measuring comprises:
        projecting a light beam through the fluid from a first side of the exhaust stream, wherein the light beam is incident on a reflector on an opposite side of the exhaust stream such that optical energy from the light beam is reflected by the reflector toward a receiver on the first side of the exhaust stream as a return beam of optical energy, wherein primarily optical energy of the return beam that is scattered over a range of near-forward angles by particulate matter in the fluid reaches the receiver, and wherein at least a portion of the fluid is present between the reflector and the receiver;
    measuring a second property of the particulate matter in the fluid;
    calculating the mass loading of the particulate matter in the fluid based on the near forward scatter and the second property.

26. The method of claim 25, wherein the second property is backscatter caused by the particulate matter in the fluid.

27. The method of claim 25, wherein the second property is extinction caused by the particulate matter in the fluid.

28. The method of claim 25, further comprising:
    measuring a third property of the particulate matter; and
    calculating includes calculating the mass loading of the particulate matter in the fluid based on the near forward scatter, the second property and the third property.

29. The method of claim 28, wherein:
    the second property includes backscatter caused by the particulate matter in the fluid; and
    the third property includes extinction caused by the particulate matter in the fluid.

30. The method of claim 25, wherein the fluid is part of an exhaust gas stream, and wherein the exhaust gas stream is generated by a process.

31. The method of claim 30, further comprising:
    measuring a second property of the exhaust gas stream; and
    calculating includes calculating the mass loading of the particulate matter in the fluid based on the near forward scatter and the second property of the exhaust gas stream.

32. The method of claim 30, further comprising:
    measuring a property of the process; and
    calculating includes calculating the mass loading of the particulate matter in the fluid based on the near forward scatter and the property of the process.

33. A method of measuring mass loading of particulate matter in a fluid, comprising:
    measuring near forward scatter caused by particulate matter in the fluid;
    measuring extinction caused by the particulate matter in the fluid;
    measuring a third property of the particulate matter; and
    calculating the mass loading of the particulate matter in the fluid based on the near forward scatter, the extinction and the third property.

34. The method of claim 33, wherein
    the second property includes backscatter caused by the particulate matter in the fluid.

35. The method of claim 1, wherein a face of the front portion of the reflector is non-orthogonal to the direction of the light beam.

* * * * *

UNITED STATES PATENT AND TRADEMARK OFFICE
CERTIFICATE OF CORRECTION

PATENT NO. : 7,224,455 B2
APPLICATION NO. : 10/857548
DATED : May 29, 2007
INVENTOR(S) : Myers et al.

Page 1 of 1

It is certified that error appears in the above-identified patent and that said Letters Patent is hereby corrected as shown below:

COLUMN 9

Line 53, equation 3 should read

-- $z_1(x_1) = b_0 + b_1*x_1 + b_2*x_1^2 + b_3*x_1^3 + b_4*x_1^4 + b_5*x_1^5$ --.

Signed and Sealed this

Twenty-second Day of January, 2008

JON W. DUDAS
*Director of the United States Patent and Trademark Office*